(12) United States Patent
Dubey Pradip et al.

(10) Patent No.: US 10,683,250 B2
(45) Date of Patent: Jun. 16, 2020

(54) MANUFACTURING PROCESS FOR DIHYDROXYDIPHENYLMETHANE WITH HIGH SELECTIVITY FOR 2,4'-DIHYDROXYDIPHENYLMETHANE

(71) Applicant: Aditya Birla Chemicals (Thailand) Ltd., Bangkok (TH)

(72) Inventors: Kumar Dubey Pradip, Bangkok (TH); Alok Khullar, Bangkok (TH); Thipa Naiyawat, Bangkok (TH); Kamonsun Visatsingh, Bangkok (TH); Patcharin Samuthsen, Bangkok (TH); Pankaj Mathure, Bangkok (TH)

(73) Assignee: ADITYA BIRLA CHEMICALS (THAILAND) LTD. (TH)

( * ) Notice: Subject to any disclaimer, the term of this patent is extended or adjusted under 35 U.S.C. 154(b) by 403 days.

(21) Appl. No.: 15/023,334

(22) PCT Filed: Sep. 20, 2013

(86) PCT No.: PCT/TH2013/000049
§ 371 (c)(1),
(2) Date: Mar. 18, 2016

(87) PCT Pub. No.: WO2015/041614
PCT Pub. Date: Mar. 26, 2015

(65) Prior Publication Data
US 2016/0229775 A1   Aug. 11, 2016

(51) Int. Cl.
*C07C 37/20*   (2006.01)
(52) U.S. Cl.
CPC .................... *C07C 37/20* (2013.01)
(58) Field of Classification Search
CPC .................................................. C07C 37/20
See application file for complete search history.

(56) References Cited

U.S. PATENT DOCUMENTS

| | | | |
|---|---|---|---|
| 2,617,832 | A | 11/1952 | Martin |
| 4,400,554 | A | 8/1983 | Ort |
| 4,937,392 | A | 6/1990 | Imanari et al. |
| 5,654,382 | A | 9/1997 | Dubois et al. |
| 6,492,566 | B1 | 12/2002 | Singh et al. |

FOREIGN PATENT DOCUMENTS

| | | | |
|---|---|---|---|
| CN | 102070409 A | | 5/2010 |
| CN | 102516035 A | | 6/2012 |
| JP | H0687775 A | | 3/1994 |
| JP | 08268943 A | * | 10/1996 |
| JP | 2006257026 A | | 9/2006 |
| JP | 39-26844 B2 | | 6/2007 |
| WO | 1997002306 A1 | | 1/1997 |
| WO | 2005049722 A1 | | 6/2005 |

OTHER PUBLICATIONS

Itaru et al. (English machine translation of JP 2006257026) (2006).*
Shen et al., English machine translation of CN 102516035A (Jun. 27, 2012).*
English machine translation of Okihama et al., JP-08268943-A (Year: 1996).*
International Search Report for international application No. PCT/TH2013/000049 dated Jun. 16, 2014.

* cited by examiner

*Primary Examiner* — Peter F Godenschwager
(74) *Attorney, Agent, or Firm* — Kim IP Law Group PLLC

(57) ABSTRACT

The invention relates to an improved manufacturing process for the preparation of high 2,4'-dihydroxydiphenylmethane, by a process involving reaction of phenol and formaldehyde, in the presence of an inorganic polyprotic acid. According to this process, the reaction conditions are selected to favour a high yield of dihydroxydiphenylmethane, with a relatively high concentration of the 2,4'-isomer, by using a relatively low molar excess of phenol than conventional methods.

20 Claims, No Drawings

MANUFACTURING PROCESS FOR DIHYDROXYDIPHENYLMETHANE WITH HIGH SELECTIVITY FOR 2,4'-DIHYDROXYDIPHENYLMETHANE

CROSS-REFERENCE TO RELATED APPLICATIONS

This application is a U.S. national phase application under U.S.C. § 371 of International Application No. PCT/TH2013/000049 filed on Sep. 20, 2013, the entire disclosure of which is hereby incorporated by reference in its entirety.

BACKGROUND OF THE INVENTION

Field of the Invention

The present invention relates to an improved process for manufacturing bis-(hydroxyphenyl)methanes. More particularly, the present invention is related to a process with improved selectivity for a 2,4'-bis(hydroxyphenyl)methane isomer and overall improved productivity due to a low molar ratio of phenol to formaldehyde, at a high reaction temperature, workable within an atmospheric pressure range. The present invention, with its higher selectivity for 2,4'-bis-(hydroxyphenyl)methane, is useful for making some specialty non-crystallizing grades of novolak-based epoxy resins on an industrial scale.

The present process comprises reacting high purity as well as recovered phenol, containing water, from same process, with formaldehyde in presence of inorganic acidic catalyst at specific range of reaction temperatures 85-100 degree C. which favours high ortho-para isomer despite lower phenol:formaldehyde ratio leading to higher productivity & easy recyclability of spent catalyst.

Description of Prior Art

Conventional bisphenol F and novolac resins are prepared from phenolic compounds and formaldehyde in the presence of an acidic catalyst like $H_2SO_4$ or oxalic acid. Such resins may have a relatively high proportion of para-para and ortho-para methylene bridges, as illustrated below.

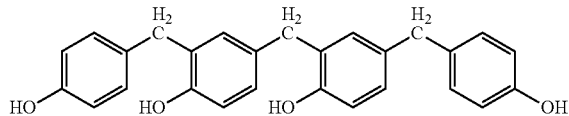 [SMILES: Oc1ccc(Cc2ccc(O)c(Cc3ccc(O)c(Cc4ccc(O)cc4)c3)c2)cc1]

High ortho novolac resins are characterized by ortho/ortho methylene bridges and have a much greater speed of curing with hardeners like hexamethylene tetraamine.

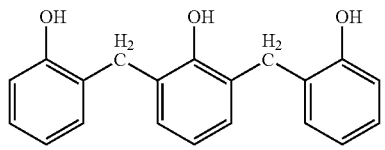 [SMILES: Oc1ccccc1Cc1cccc(Cc2ccccc2O)c1O]

4,4'-Dihydroxydiphenylmethane is useful starting material for the production of polycarbonate resins, polyester resins, and epoxy novolac resin, and as a modifier and stabilizer for phenol resins [U.S. Pat. No. 6,492,566].

To meet end application requirements, a desired blend of properties, like curing speed, reactivity, and other end properties like softening point, Tg, control of the isomer ratio between ortho-ortho, ortho-para and para-para, and the monomer:oligomer ratio becomecritical. Selection of catalyst type has a detrimental effect on the isomer ratio and overall monomer content, as well as dimer and oligomer ratios and/or proportions.

Several methods are known for preparing dihydroxydiphenylmethanes. Conventional methods comprising reacting phenol with dimethylol urea in the presence of hydrochloric acid (40% HCl) or glacial acetic acid can afford 47.9% yield of diphenylolmethane [U.S. Pat. No. 2,617,832].

JP-B-39-26844 discloses a method for reacting phenol with formaldehyde in the presence of urea, filtering the solid thus precipitated, and recrystallizing the same from water.

U.S. Pat. No. 4,400,554 discloses a method for reacting phenol with formaldehyde in the presence of aqueous $H_3PO_4$. An object of this invention is to afford a high concentration of 4,4'-isomer. Typical 4,4'-, 2,4'-, and 2,2'-dihydroxydiphenylmethanes in a ratio of 55:37:8 have been reported. The molar ratio of phenol to formaldehyde is in the range of about 3:1 to 20:1.

U.S. Pat. No. 4,937,392 discloses a process for reacting phenol with formaldehyde with catalysts such as oxalic acid and activated clay at molar ratios of phenol:formaldehyde (P:F) starting from 8 to 25. The range of individual isomers of bis-(hydroxyphenyl)methane varies from 29.5%-44.5% of the 4,4' isomer, 40.5%-50.3% of the 2,4' isomer, and 16.5%-20.6% of the 2,2' isomer. An object of this invention is to get high selectivity for 4,4'-dihydroxydiphenylmethane relative to 2,4'-dihydroxydiphenylmethane.

To lower the content of oligomers, including trimers, preferred phenol:formaldehyde molar ratio can be as high as 20:1 and 25:1. However, the process has several disadvantages from an industrial point of view. For example, the process has the drawback of using a very high phenol:formaldehyde ratio, and use of a heterogeneous catalyst like clay which, from the industrial point of view, is disadvantageous since it calls for an additional unit operation like filtration.

U.S. Pat. No. 6,492,566 discloses a process for reacting phenol with formaldehyde in presence of a microporous alumino-silicate zeolite catalyst to afford a high proportion of 2,4'-dihydroxydiphenylmethane (about 46%-53%), and lower proportions of 2,2'-dihydroxydiphenylmethane (about 15%-33%) and 4,4'-dihydroxydiphenylmethane (about 13%-27%). However, the process has certain disadvantages. Although microporous zeolites can provide a high selectivity of 2,4'-dihydroxydiphenylmethane, the percent conversion is very low.

Use of a high pressure autoclave, a heterogeneous catalyst filtration step, and lower percent conversions to dihydroxydiphenylmethane (on the order of 14% to 23%), when the molar ratio of phenol to formaldehyde is between from 5:1 to 10:1, makes this process industrially unattractive.

U.S. Pat. No. 5,654,382 and WO9702306 disclose that bisphenol F containing a higher proportion of 2,2'- and 2,4'-isomers lowers the melt viscosity and solution viscosity of bisphenol F epoxy resin. However, both patents are silent on any method to increase the proportions of the 2,2'- and 2,4'-isomers of bisphenol F.

CN 102070409A discloses the preparation of bisphenol F with a high proportion of ortho isomers, but the reaction procedure involves usage of high purity molten phenol, dosing of formaldehyde in two shots at two different temperature conditions (70° C. and 60° C., respectively), and a relatively high phenol to formaldehyde ratio on the order of 12-25, which makes this process industrially unattractive.

Moreover, this patent is silent on the impact of the high monomer content in general and the 2,4'-isomer specifically on the crystallization resistance properties of bisphenol F epoxy resin. Also injecting ammonia in the molten phenol before charging the phosphoric acid catalyst further adds one additional step which makes this process industrially unattractive.

In the prior art, wherever oxalic acid or phosphoric acid is used as a catalyst, to get a relatively high percentage of 2,4'-dihydroxydiphenylmethanes (e.g., >45%), a molar ratio of phenol:formaldehyde exceeding 12-25:1 is generally required, which makes the manufacturing process unattractive due to high vessel occupancy and/or volume in the reactor by the phenol, the relatively high energy cost for recovery of un-reacted phenol, and the relatively low productivity per batch from the reactor.

CN102516035A discloses a process for the preparation of bisphenol F with a high content of ortho isomer(s) and with a low phenol to formaldehyde ratio, but suffers the disadvantage of using an organic monobasic or dibasic co-catalyst with the inorganic acidic catalyst. This makes this process industrially less attractive, as recovery of the catalyst(s) from the spent acid catalyst stream is relatively complex, and usage of an organic acid as co-catalyst causes an increased load of salts in the organic stream during the neutralization step.

The use of dihydroxydiphenylmethane with a relatively high percentage of 2,4'-dihydroxydiphenylmethane and a low oligomer content is preferred as a starting material for high performance bisphenol F base epoxy resins. These epoxy resins are used for civil applications, as they have high workability and ease of transportation in cold regions due to a very low crystallization tendency. The demand for such specialty bisphenol F based epoxy resins is increasing day by day.

OBJECTS OF THE INVENTION

In view of above mentioned limitations of prior art processes (e.g., the use of heterogeneous catalysis, low productivity due to relatively high phenol to formaldehyde ratios, low selectivity for 2,4'-dihydroxydiphenylmethane, etc.), an industrial process for production of dihydroxydiphenylmethane with high selectivity for the 2,4'-dihydroxydiphenylmethane isomer from the condensation of phenol and formaldehyde was developed.

It is an object of the present invention to solve the above-mentioned problems of low productivity resulting from a high phenol:formaldehyde ratio using an industrial process which is performed with a relatively low phenol: formaldehyde ratio (e.g., from 6:1 to 15:1).

It is a further object of the present invention to obtain a higher selectivity for 2,4'-dihydroxydiphenylmethane at a relatively high temperature range (e.g., 85-100° C.), at atmospheric pressure.

It is an even further object of the present invention to increase the selectivity of 2,4'-dihydroxydiphenylmethane production without using a heterogeneous catalyst or any co-catalyst, thereby avoiding certain additional unit operation(s) such as filtration, and still achieve excellent recovery and/or recycling of the catalyst.

Another object of present invention is to provide improved process conditions for making dihydroxydiphenylmethane with consistent results, irrespective of the purity of the input phenol (e.g., in the range of 99 wt % to 75 wt %, in the case of recovered phenol containing up to 25 wt % reaction water), thereby reducing the dependence on high purity molten phenol and avoiding an additional phenol refining step to achieve high 2,2'- and 2,4'-isomer ratios and/or proportions.

Yet another object of present invention is to provide improved process conditions which allow for single step addition of catalyst at a fixed temperature, thereby avoiding ramping the reaction temperature profile during the catalyst charging step.

The inventors of this process have conducted intensive studies to accomplish the foregoing objects, and have found that one or more of these objects can be achieved through an energy efficient process for the preparation of dihydroxydiphenylmethanes, with high selectivity for 2,4'-dihydroxydiphenylmethane, and lower reaction time(s), by conducting the process at a relatively high temperature, which favours formation of the 2,2'- and 2,4'-isomers, without any need for an acidic or basic co-catalyst charged separately or prepared in-situ.

SUMMARY OF THE INVENTION

The present invention relates to a manufacturing process for dihydroxydiphenylmethane having preferential selectivity for formation of 2,4'-dihydroxydiphenylmethane, comprising reacting phenol containing up to 25 wt % water with formaldehyde, at a relatively low molar ratio of phenol to formaldehyde, in the presence of an acid catalyst, in a heterogeneous phase, at a temperature of from 85-100° C., at atmospheric pressure. The present process can use high purity phenol as well as phenol recovered from the present process (e.g., recycled phenol).

In addition, the present invention relates to an improved manufacturing process for the preparation of dihydroxydiphenylmethanes with high selectivity for 2,4'-dihydroxydiphenylmethane, which is critical to some of the characteristic properties of specialty grade Bisphenol F epoxy resins. These properties are critical for usability in countries that have low temperature conditions.

The process of the present invention has many advantages, for example:
(1) It gives a high yield of dihydroxydiphenylmethanes, and particularly 2,4'-dihydroxydiphenylmethane in high selectivity, when the reaction is done at an elevated temperature and at atmospheric pressure.
(2) The process can be completed in the absence of any solvent, which facilitates the easy and economical recovery of excess phenol.
(3) The process can yield a high proportion of the 2,4'-isomer of bisphenol F, using a phenol:formaldehyde molar ratio of from 6:1 to 15:1. Avoiding a large excess of phenol makes this process attractive in terms of increased productivity per batch and lower energy consumption for recovering excess phenol.
(4) The process can yield a high proportion of 2,4'-isomer without any need to change the temperature profile during catalyst charging, which also makes it industrially attractive.
(5) The process can yield a high 2,4-isomer ratio or proportion using a single addition of catalyst and/or formaldehyde.
(6) The process uses a relatively high temperature, on the order of 85-100° C. (e.g., 85-95° C.), which favors forming a high proportion of 2,2'- and 2,4'-isomers and facilitates conversion of the 4,4'-isomer preferentially to oligomer (preferably in small quantities), thereby leading to an overall increase in the ratio of o,p and o,o isomers to p,p isomer, preferably with not more than 9-10% oligomer, which imparts excellent crystallization resistance in bisphenol F epoxy resins.

(7) The process may further involve avoiding contamination of acidic catalyst vapours or traces in the recovered phenol.

(8) Recovered phenol of low purity (e.g., as low as 75 wt %) and containing reaction water and water contributed by aqueous formaldehyde can be used without further purification.

DETAILED DESCRIPTION OF THE INVENTION

The present invention relates to a process for manufacturing dihydroxydiphenylmethane having relatively high preferential selectivity for 2,4'-dihydroxydiphenylmethane, comprising reacting phenol with formaldehyde, using a relatively low phenol/formaldehyde molar ratio, in the presence of a polyprotic inorganic acid catalyst, in a heterogeneous phase at a temperature of from 85 to 100° C. The phenol may have high purity (e.g., ≥99 wt %) or be recovered or recycled from the present process.

In the context of the present application, the terms "high purity phenol" may refer to a fresh phenol having a purity of at least 99 wt %, and "recovered phenol" may refer to phenol recovered from previous batches of the present process containing up to 25% moisture (wt./wt.) from reaction by-product water and/or water from aqueous formaldehyde (which may be combined together from penultimate batches) without any refining. However, the phenol component should contain at least 75 wt % phenol.

In the context of the present application, the term "low phenol/formaldehyde ratio" may refer to a ratio in the range of 6-15 (e.g., from 6:1 to 15:1), for example from 6:1-12:1 and preferably 6:1-10:1. When the phenol/formaldehyde ratio is in the range of from 6:1 to 12:1, the present process provides a desired 2,2':2,4':4,4'-dihydroxydiphenylmethane ratio, which is useful for specialty bis-F phenol-based epoxy resins, the glycidyl ethers of which are suitable for use in colder regions.

According to one aspect of the present invention, formaldehyde is added at a temperature of 85-100° C.

According to the present application, the acidic catalyst may refer to an inorganic acid catalyst that is very sparingly miscible with the organic phase. For example, the acid catalyst may be a weak polyprotic acid having a first pKa in the range of 2-3.5. Acid catalysts with a pKa in the range of 2-3.5 can provide a yield of monomer (i.e., bis(hydroxyphenyl)methane) in the range of 80-90%. Acidic catalysts with a lower pKa may lead to higher oligomer formation, and acidic catalysts with a higher than specified pKa may cause a slow reaction. The acid catalyst can be a combination of oxalic acid and phosphoric acid. Polyprotic inorganic acids like phosphoric acid are preferred catalysts.

In one embodiment, the molar ratio of acidic catalyst to formaldehyde during the reaction is in the range of 2.7-3.

According to another embodiment of the invention, the reaction is carried out at a temperature of 85° C. to 100° C. at atmospheric pressure. When the reaction temperature is lower than 85° C., the reaction may proceed at a relatively slow rate and lead to a lower overall proportion of ortho isomers and a lower overall monomer content, which is undesirable in practice for non-crystallizing bisphenol F epoxy resins. In addition, 4,4'-dihydroxydiphenylmethane may be formed in a relatively high proportion. When the reaction temperature exceeds 100° C., the content of oligomers, including trimers and higher oligomers, increases, which is undesirable and also disturbs the desired isomer ratio. A reaction temperature in the range of 85 to 100° C. with a molar ratio of phenol/formaldehyde in the range of 6:1-10:1 may be most suitable for forming bis(hydroxyphenyl)methane for non-crystallizing bisphenol F epoxy resins.

The present process is suitable for industrial-scale processes for manufacturing dihydroxydiphenylmethane with a high ortho content, as spent acid can be recovered by phase separation and recycled for use in subsequent reaction(s).

According to another embodiment of the present invention, excess phenol is recovered by distillation. The distilled phenol is suitable for recycling and/or reuse in the present process.

The isomer ratio of para-para/ortho-para/ortho-ortho isomers of dihydroxydiphenylmethane obtained from the present process is normally in the range of 34-36:44-46:7-8, respectively. An overall percentage of ortho-ortho plus ortho-para isomers is generally greater than 58% of the total monomer content. This is quite useful for a desired balance between the reactivity and flow properties of the bisphenol F based epoxy resin derived from dihydroxydiphenylmethane produced using the process of the invention.

The above embodiment(s) of the present invention facilitate a high selectivity for 2,4'-bis(hydroxyphenyl)methane, at atmospheric pressure, thereby reducing the dependence on or need for a high pressure autoclave.

Further embodiments of the present invention comprise recovery of the acid catalyst(s) that separate out as a second phase, typically at the bottom of the organic layer, and the second phase is physically removed from the reactor (typically, the bottom of the reactor). This step of separating the acidic catalyst permits recycling of the polyprotic catalyst(s) for recycling and multiple reuse.

The traces of acidic catalyst left in the organic phase can be neutralized to a salt with sodium carbonate or other suitable base. The neutralization is complete when an aqueous solution of sodium carbonate or other base used to neutralize the trace acid has a pH of 6-6.5 after the neutralization, thereby causing minimum contamination of organic layer with the acid catalyst and the salt(s). This step is useful for maintaining a desired isomer ratio during the phenol recovery.

The present process for manufacturing dihydroxydiphenylmethane may further comprise recovering un-reacted phenol and recycling the recovered, un-reacted phenol. The obtained dihydroxydiphenylmethane has a high proportion of 2,4'-dihydroxydiphenylmethane may be used without further purification as a starting raw material to produce bisphenol F epoxy resins.

The process of the present invention may be conducted without azeotropic removal of water. The water content in the present reaction may be 20-23% by weight.

Dihydroxydiphenylmethane obtained from a process of present invention provides 4,4'-, 2,4'-, and 2,2'-dihydroxydiphenylmethane in a molar ratio of 34-36:44-46:7-8, respectively, wherein the overall percentage of monomer (e.g., bis(hydroxyphenyl)methane) can be >85%, and perhaps as high as 88-90% by moles or by weight. The combined percentage of 2,2'-dihydroxydiphenylmethane and 2,4'-dihydroxydiphenylmethane monomers, based on the total of all monomers, is more than 58% (e.g., by moles), which is useful to get very low crystallizing epoxy glycidyl ethers of the dihydroxydiphenylmethane product mixture, which facilitates easy processability of the epoxy resins in low temperature regions. 2,2'-Dihydroxydiphenylmethane in the overall monomer composition can be maintained below 10% (e.g., by moles).

Example 1

To a 1000 ml flask were added 77% phenol and an acid catalyst as shown in Table 1.1 below. The mixture was stirred and heated up to 85-100° C. under a nitrogen atmosphere. 37% formaldehyde (FDH) was added at a uniform rate and kept stirring until the reaction was completed. The reaction mixture was cooled to room temperature. In the case of phosphoric acid as catalyst, the aqueous layer is separated before neutralization. Residual acid in the organic layer was neutralized with sodium bicarbonate, and then the excess phenol was removed. The products were analyzed by high performance liquid chromatography (HPLC).

Inorganic polyprotic acidic catalyst alone, and, in combination with organic acids of different pKa values as shown in Table 1.1, were studied, and the results are shown in table 1.2.

TABLE 1.1

| Acids | pKa |
|---|---|
| Phosphoric acid | 2.12, 7.21, 12.32 |
| Oxalic acid | 1.25, 4.14 |
| Acetic acid | 4.792 |

TABLE 1.2

| | Example No: | | | | |
|---|---|---|---|---|---|
| | 1 | 2 | 3 | 4 | 5 |
| Phenol/FDH by mole | 25 | 6 | 6 | 6 | 6 |
| 77% Phosphoric acid (Moles, based on FDH) | — | — | 3 | 3 | — |
| Oxalic acid (% based on phenol) | 0.1 | 0.1 | 0.1 | — | — |
| Acetic acid (Moles, based on FDH) | — | — | — | — | 6 |
| Products | | | | | |
| Yield (% based on FDH) | 95.5 | 81.1 | 95.8 | 96.3 | Too slow reaction |
| 4,4'-dihydroxydiphenylmethane (%) | 32.1 | 24.54 | 35.74 | 35.8 | |
| 2,4'-dihydroxydiphenylmethane (%) | 45.5 | 32.65 | 43.21 | 45.1 | |
| 2,2'-dihydroxydiphenylmethane (%) | 11.2 | 15.21 | 7.31 | 7.1 | |
| Total dihydroxydiphenylmethane (%) | 88.8 | 72.4 | 86.26 | 88.0 | |
| Presence of organic salts in organic layer | Yes | Yes | Yes | No | Yes |

As the results from Table 1.2 show, it is clearly seen that the processes representative of present invention (examples 3-4) have similar or higher productivity than the comparative examples (examples 1-2 and 5). Example 4 has the further advantage of no organic salts in the organic layer. Example 2 with oxalic acid alone showed lower overall monomer content compared to Example 4 which used only phosphoric acid and Example 3 which used a combination of phosphoric acid and oxalic acid.

Example 2 le;2qTo a 1000 ml flask were added 305 g of 77% phenol and 159 g of 77% phosphoric acid. The mixture was stirred and heated up to a temperature of from 30 to 100° C. (see Table 2 below) under a nitrogen atmosphere. 33.8 g of 37% formaldehyde was added at a uniform rate and kept stirring until the reaction was completed. The reaction mixture was cooled to room temperature. The aqueous layer was separated. Residual acid in the organic layer was neutralized with sodium bicarbonate and then the excess phenol was removed. The products were analyzed by high performance liquid chromatography (HPLC). The reaction temperature was kept from 30 to 100° C. The results are listed in Table 2.

TABLE 2

| Example No: | 6 | 7 | 8 | 9 | 10 | 4 |
|---|---|---|---|---|---|---|
| Formaldehyde addition temperature (° C.) | 30 | 45 | 65 | 85 | 100 | 85 |
| Reaction temperature (° C.) | 30 | 45 | 65 | 85 | 100 | 100 |
| Reaction time (hrs) | 48 | 4 | 3 | 3 | 1 | 1 |
| Products | | | | | | |
| Yield (% based on FDH) | 78.7 | 92.0 | 92.0 | 94.5 | 94.3 | 96.3 |
| 4,4'-dihydroxydiphenylmethane (%) | 38.0 | 38.1 | 36.1 | 36.0 | 34.4 | 35.8 |
| 2,4'-dihydroxydiphenylmethane (%) | 35.6 | 39.4 | 43.3 | 44.8 | 45.4 | 45.1 |
| 2,2'-dihydroxydiphenylmethane (%) | 5.1 | 5.2 | 6.3 | 7.3 | 7.8 | 7.1 |
| Total dihydroxydiphenylmethane (%) | 78.7 | 82.7 | 85.6 | 88.2 | 87.6 | 88.0 |

As shown in Table 2, the processes according to present invention, carried out at a reaction temperature of 45-100° C., have much higher yield than the comparative example(s). A reaction temperature above 100° C. requires a high pressure autoclave and makes the process complex. At temperatures less than 85° C., overall dihydroxydiphenyl methane production and the combined % of ortho isomers shows a downward trend, and may not be suitable for low crystallization grade Bisphenol F epoxy resins.

Example 3

To a 1000 ml flask were added 305-610 g of 77% phenol and 159 g of 77% phosphoric acid. The mixture was stirred and heated up to 85-100° C. under a nitrogen atmosphere. 33.8 g of 37% formaldehyde was added at a uniform rate and kept stirring until the reaction was completed. The reaction mixture was cooled to room temperature. The aqueous layer was separated. Residual acid in the organic layer was neutralized with sodium bicarbonate and then the excess phenol was removed. The products were analyzed by high performance liquid chromatography (HPLC). The molar ratio of phenol to formaldehyde was varied from 6:1 to 12:1. The results are listed in Table 3.

TABLE 3

| | Example No: | | |
|---|---|---|---|
| | 4 | 11 | 12 |
| Molar ratio of phenol/FDH Product | 6:1 | 9:1 | 12:1 |
| Yield (% based on FDH) | 96.3 | 94.9 | 95.9 |
| 4,4'-dihydroxydiphenylmethane (%) | 35.8 | 36.15 | 33.7 |
| 2,4'-dihydroxydiphenylmethane (%) | 45.1 | 43.77 | 44.9 |
| 2,2'-dihydroxydiphenylmethane (%) | 7.1 | 8.17 | 8.8 |
| Total dihydroxydiphenylmethane (%) | 88.0 | 88.09 | 87.5 |

The results of Table 3 show that the process of the present invention has high productivity and high ortho product selectivity even when the reaction is carried out at a relatively low phenol/formaldehyde ratio.

Example 4

To a 1000 ml flask, were added 305 g of 77% phenol and 69-159 g of 77% phosphoric acid. The mixture was stirred and heated up to 85-100° C. under a nitrogen atmosphere. 33.8 g of 37% formaldehyde (FDH) was added at a uniform rate and kept stirring until the reaction was completed. The reaction mixture was cooled to room temperature. The aqueous layer was separated. Residual acid in the organic layer was neutralized with sodium bicarbonate, and then the excess phenol was removed. The products were analyzed by high performance liquid chromatography (HPLC). The molar ratio of phosphoric acid to formaldehyde was varied from 1.3:1 to 3.0:1. The results are listed in Table 4 below.

TABLE 4

| | Example No. | | |
|---|---|---|---|
| | 4 | 13 | 14 |
| Molar ratio of $H_3PO_4$/FDH BPF product | 3.00 | 2.73 | 1.30 |
| Yield (% based on FDH) | 96.3 | 96.0 | 95.6 |
| 4,4'-dihydroxydiphenylmethane (%) | 35.8 | 35.1 | 30.6 |
| 2,4'-dihydroxydiphenylmethane (%) | 45.1 | 45.4 | 39.4 |
| 2,2'-dihydroxydiphenylmethane (%) | 7.1 | 7.2 | 7.5 |
| Total dihydroxydiphenylmethane (%) | 88.0 | 87.7 | 77.53 |

The above examples summarized in Table 4 show that higher phosphoric acid to formaldehyde ratios (e.g., 2.5 to 3) favours a formation of monomer in a higher percentage overall; along with a relatively high selectivity for the combined ortho isomers in the overall total monomer content.

Example 5

To a 1000 ml flask were added 248 g of 95% phenol, 159 g of 77% phosphoric acid and 39-68 g of water. The mixture was stirred and heated up to 85-100° C. under a nitrogen atmosphere. 33.8 g of 37% formaldehyde was added at a uniform rate and kept stirring until the reaction was completed. The reaction mixture was cooled to room temperature. The aqueous layer was separated. The organic layer was neutralized with sodium bicarbonate, and then the excess phenol was removed. The products were analyzed by high performance liquid chromatography (HPLC). The water content in the reaction mixture was varied from 12 to 23 wt %. The results are listed in Table 5.

TABLE 5

| | Example No.: | | |
|---|---|---|---|
| | 4 | 15 | 16 |
| % Water in reaction (by weight) Products | 23 | 20 | 12 |
| Yield (% based on FDH) | 96.3 | 95.2 | 95.6 |
| 4,4'-dihydroxydiphenylmethane (%) | 35.8 | 31.2 | 33.2 |
| 2,4'-dihydroxydiphenylmethane (%) | 45.1 | 45.9 | 37.6 |
| 2,2'-dihydroxydiphenylmethane (%) | 7.1 | 8.1 | 8.2 |
| Total dihydroxydiphenylmethane (%) | 88.0 | 85.2 | 79.0 |

The above experiments summarized in Table 5 confirm that a higher water content (between 10-20 wt. %) in the reaction mixture provides a higher overall percentage of monomer with a higher percentage (>55%) or proportion of combined o,o+o,p isomers of the total amount of monomer.

Example 6

To a 1000 ml flask were added 305 g of 77% phenol and 159 g of 77% phosphoric acid. The mixture was stirred and heated up to 85-100° C. under a nitrogen atmosphere. 13.6 g of 92% para-formaldehyde was added in portions and kept stirring until the reaction was completed. The reaction mixture was cooled to room temperature. The aqueous layer was separated. Residual acid in the organic layer was neutralized with sodium bicarbonate, and then the excess phenol was removed. The product was analyzed by high performance liquid chromatography (HPLC). The results are listed in Table 6 below.

TABLE 6

| | Example No.: | |
|---|---|---|
| | 4 | 17 |
| Formaldehyde Products | 37% FDH | 92% p-FDH |
| Yield (% based on FDH) | 96.3 | 96.6 |
| 4,4'-dihydroxydiphenylmethane (%) | 35.8 | 37.8 |
| 2,4'-dihydroxydiphenylmethane (%) | 45.1 | 44.4 |
| 2,2'-dihydroxydiphenylmethane (%) | 7.1 | 7.0 |
| Total dihydroxydiphenylmethane (%) | 88.0 | 89.2 |

The above experiments in Table 6 confirm that such as in the present process, either recovered phenol from previous batches, which can contain 20-25 wt. % moisture, or dilute fresh phenol can be used, with formaldehyde solution as well as alternate sources of formaldehyde paraformaldehyde, without compromising monomer yield. This makes the present process commercially more attractive. The ratio of the percentage of ortho isomers to the total yield of monomers was >58%.

Example 7

Preparation of Diglycidyl Ether of Dihydroxydiphenylmethane 100 g of Bisphenol F containing up to 88% of dihydroxydiphenylmethane is dissolved in 277.5 g of epichlorohydrin in a 1000 ml flask. 4.0 g of 50% sodium hydroxide is added at 50° C. The solution is then maintained at 60-62° C. for 3 hours. 74 g of 50% sodium hydroxide is added dropwise at 63-65° C. under vacuum for 2 hours. Water in the reaction mixture is removed by azeotropic distillation with epichlorohydrin, then excess epichlorohydrin is distilled out. 230 g of toluene and 190 g of water are added: The mixture is stirred for 15 minutes at 60-65° C., and then the aqueous phase (brine) is separated. The organic layer is neutralized by diluted phosphoric acid solution and subsequently with water. Bisphenol F epoxy resin is obtained after distilling out the toluene.

The basic properties of the bisphenol F epoxy resin are analyzed. Crystallization resistance is checked by an in-house developed method. For example, 20 g of bisphenol F epoxy resin is blended with 0.1 g of pure bisphenol F diglycidyl ether and 1 g of a corresponding long chain monoglycidyl ether. The samples, are cycled daily between a refrigerator at 10° C. for 16 hours and room temperature for 8 hours (Monday to Friday), and are stored at 10° C. (Saturday-Sunday) over the course of 90 days. The sample appearance is observed daily. The results are listed in Table 7.

TABLE 7

|  |  | Example No.: | | |
| --- | --- | --- | --- | --- |
|  |  | 16 | 17 | 18 |
| Bisphenol F | 4,4'-dihydroxydiphenyl-methane (%) | 35.8 | 36.5 | 45.2 |
|  | 2,4'-dihydroxydiphenyl-methane (%) | 45.1 | 39.7 | 32.4 |
|  | 2,2'-dihydroxydiphenyl-methane (%) | 7.1 | 7.6 | 9.9 |
|  | Total dihydroxydiphenyl-methane (%) | 88.0 | 83.8 | 87.5 |
|  | Ortho isomers (%) | 59.3 | 56.4 | 48.3 |
| Bisphenol F epoxy resin | Epoxy equivalent weight (g/eq) | 173.4 | 175.3 | 172.8 |
|  | Hydrolyzable chlorine (wt %) | 0.065 | 0.054 | 0.072 |
|  | Viscosity at 25° C. (cPs) | 4013 | 4304 | 4304 |
|  | Crystallization resistance (days) | >90 | 11 | 2 |

As shown in Table 7, when the bisphenol F based epoxy resin is produced according to the present process above, the higher combined percentage of ortho isomers as a percentage of the total monomer (>58%) gives excellent crystallization resistance.

What is claimed is:

1. A process for manufacturing dihydroxydiphenylmethane, comprising (1) reacting phenol with formaldehyde in the presence of a polyprotic inorganic acid catalyst in a heterogeneous phase without any co-catalyst, at a temperature of from 85 to 100° C. and (2) recovering the polyprotic inorganic acid catalyst.

2. The process according to claim 1, wherein the phenol is 75-99 wt % fresh phenol or recovered phenol, containing up to 25% water.

3. The process according to claim 1, further comprising adding the formaldehyde to the phenol and polyprotic inorganic acid catalyst at 85-100° C.

4. The process according to claim 2, further comprising recovering unused phenol with up to 25% wt/wt of water, and reusing or recycling the recovered phenol.

5. The process according to claim 1, wherein a ratio of phenol to formaldehyde is from about 6:1 to 15:1.

6. The process according to claim 1, wherein a ratio of phenol to formaldehyde is from about 6:1 to 12:1.

7. The process according to claim 1, wherein a ratio of phenol to formaldehyde is from about 6:1 to 10:1.

8. The process according to claim 1, wherein the polyprotic inorganic acid catalyst is sparingly soluble in an organic phase.

9. The process according to claim 1, wherein the polyprotic inorganic acid catalyst is a weak polyprotic acid catalyst.

10. The process according to claim 1, wherein the polyprotic inorganic acidic catalyst has a first pKa in a range of 2-3.5.

11. The process according to claim 1, wherein the polyprotic inorganic acid catalyst is phosphoric acid.

12. The process according to claim 1, wherein a molar ratio of the polyprotic inorganic acid catalyst to formaldehyde is in a range of 2.7-3.

13. The process according to claim 1, wherein the temperature is in a range of 85° C. to 95° C.

14. The process according to claim 1, wherein the temperature is in a range of 85° C. to 90° C.

15. The process according to claim 1, further comprising recovering the acid catalyst by separating the acid catalyst as a second phase, and physically removing the recovered acid catalyst from a bottom of a reactor.

16. The process according to claim 1, further comprising (3) recovering the polyprotic inorganic acid catalyst, and (4) neutralizing traces of any polyprotic inorganic acid catalyst remaining in an organic phase with a mild base.

17. The process according to claim 16, wherein the mild base is sodium carbonate and is added to the organic phase until a pH is 6-6.5.

18. The process according to claim 1, wherein the dihydroxydiphenylmethane has a ratio of combined o,o and o,p isomers to total dihydroxydiphenylmethane monomers above 58%.

19. The process according to claim 18, wherein the ratio of combined o,o and o,p isomers to total monomers imparts a crystallization resistance of greater than 90 days to an epoxy resin made using the dihydroxydiphenylmethane.

20. The process according to claim 1, using a molar ratio of phenol to formaldehyde of from about 6:1 to about 12:1 and having a preferential selectivity for 2,4'-dihydroxydiphenylmethane.

* * * * *